United States Patent [19]

Philipp et al.

[11] 4,033,977
[45] July 5, 1977

[54] 4H-PYRANO[4,3-d]THIAZOLE DERIVATIVES AND PROCESS THEREFOR

[75] Inventors: Adolf H. Philipp, St. Laurent; Leslie G. Humber, Dollard des Ormeaux, both of Canada

[73] Assignee: American Home Products Corporation, New York, N.Y.

[22] Filed: Oct. 1, 1975

[21] Appl. No.: 618,643

[52] U.S. Cl. .................... 260/302 F; 260/247.1 L; 260/268 H; 260/293.67; 424/270
[51] Int. Cl.² .......................................... C07D 515/00
[58] Field of Search ................................ 260/302 F

[56] References Cited

UNITED STATES PATENTS

| | | | |
|---|---|---|---|
| 2,899,430 | 8/1959 | Sprague | 260/302 F |
| 3,696,101 | 10/1972 | Litt et al. | 260/302 F |

*Primary Examiner*—R. J. Gallagher
*Attorney, Agent, or Firm*—Stephen Venetianer

[57] ABSTRACT

4H-Pyrano[4,3-d]thiazole derivatives characterized by having a 4H-pyrano[4,3-d]thiazole nucleus having a phenyl substituent at position 2 and a substituent at position 4, said substituent incorporating an acidic or basic function therein, are disclosed. The nucleus is further substituted at position 4 with a lower alkyl and may be optionally substituted in the phenyl ring. The foregoing compounds possess anti-inflammatory and antidepressant activity and methods for their preparation and use are described.

17 Claims, No Drawings

4H-PYRANO[4,3-D]THIAZOLE DERIVATIVES AND PROCESS THEREFOR

BACKGROUND OF THE INVENTION

This invention relates to novel 4H-pyrano[4,3-d]thiazole derivatives. More particularly, this invention relates to heterocycles having a 4H-pyrano[4,3-d]thiazole nucleus, to processes for their preparation, to intermediates used for the processes, to methods for using the 4H-pyrano[4,3-d]thiazole derivatives and to pharmaceutically acceptable compositions of said derivatives.

Notwithstanding the advances made during the last four decades in the development of agents for the treatment of inflammatory conditions and disorders of the central nervous system, there still remains a need for effective agents.

The 4H-pyrano[4,3-d]thiazole derivatives of this invention, with a novel ring structure, have been found to exhibit useful pharmacologic properties at doses which do not elicit undesirable side effects. Notable attributes of these properties are anti-inflammatory and antidepressant activities.

SUMMARY OF THE INVENTION

The compounds of this invention are represented by formula I

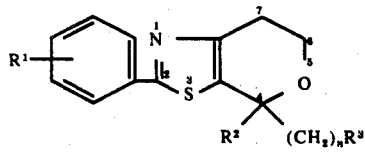

in which $R^1$ is hydrogen, halogen, lower alkyl, lower alkoxy or nitro; $R^2$ is lower alkyl; $R^3$ is COOH or $CH_2NR^4R^5$ in which $R^4$ and $R^5$ are the same or different selected from the group consisting of hydrogen and lower alkyl; and $n$ is the integer one or two.

The 4H-pyrano[4,3-d]thiazole derivatives of this invention of formula I are prepared by condensing a compound of formula II

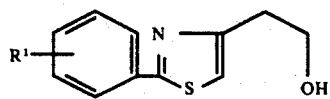

in which $R^1$ is as defined herein with a compound of formula III

wherein $R^2$ and $n$ are as defined herein and A is selected from the group consisting of
 a. $COOR^6$ in which $R^6$ is hydrogen or lower alkyl,
 b. $CONR^4R^5$ in which $R^4$ and $R^5$ are as defined herein,
 c. $CH_2OCOR^7$ in which $R^7$ is lower alkyl,
 d. $CH_2NR^4COR^8$ in which $R^4$ is as defined herein and $R^8$ is hydrogen or an alkyl containing from one to five carbon atoms, and
 e. $CH_2NR^4R^5$ in which $R^4$ and $R^5$ are as defined herein, in the presence of an acid catalyst to obtain the corresponding compound of formula IV

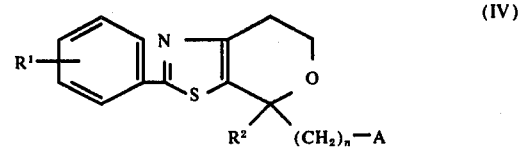

in which $R^1$, $R^2$, $n$ and A are as defined hereinbefore; followed, when said compound of formula IV is different from said compound of formula I, by transformation of said compound of formula IV to said compound of formula I by methods described herein.

More specifically, the transformation of said compound of formula IV to said compound of formula I comprises:

a. when A of said compound of formula IV is $COOR^6$ as defined above, one aspect involves hydrolyzing said compound of formula IV in which $R^6$ is lower alkyl to obtain the corresponding acid of formula I in which $R^3$ is COOH; another aspect involves subjected said acid, namely the compound of formula IV in which A is $COOR^6$ wherein $R^6$ is hydrogen which is also the compound of formula I in which $R^3$ is COOH, obtained from either the condensation or the above-noted hydrolysis reaction, to amidation with an appropriate amine of formula $NHR^4R^5$ in which $R^4$ and $R^5$ are as defined herein to give the corresponding amide (IV, A = $CONR^4R^5$), and reducing said amide with a suitable complex metal hydride to obtain the corresponding amino compound of formula I in which $R^3$ is $CH_2NR^4R^5$ wherein $R^4$ and $R^5$ are as defined herein; still another aspect involves, when A of said compound of formula IV is $COOR^6$ in which $R^6$ is hydrogen reducing said acid with a complex metal hydride to obtain the corresponding primary alcohol, converting said alcohol to a reactive intermediate such as the corresponding mesylate, tosylate or halide in which the halogen is selected from bromine, chlorine or iodine and reacting the reactive intermediate with an amine of formula $NHR^4R^5$ in which $R^4$ and $R^5$ are as defined herein to give the corresponding amino compound of formula I in which $R^3$ is $CH_2NR^4R^5$ wherein $R^4$ and $R^5$ are as defined herein;

b. when A of said compound of formula IV is $CONR^4R^5$, reducing said compound of formula IV with a complex metal hydride to obtain the corresponding amino compound of formula I in which $R^3$ is $CH_2NR^4R^5$ wherein $R^4$ and $R^5$ are as defined herein;

c. when A of said compound of formula IV is $CH_2OCOR^7$ in which $R^7$ is as defined herein, hydrolyzing said compound of formula IV with a suitable alkali to give the corresponding primary alcohol and transformation of said alcohol as described hereinabove in (a) to give the corresponding amino compound of formula I in which $R^3$ is $CH_2NR^4R^5$ wherein $R^4$ and $R^5$ are as defined herein;

d. when A of said compound of formula IV is $CH_2NR^4COR^8$ in which $R^4$ and $R^8$ are as defined herein, reducing said compound of formula IV with a complex metal hydride to obtain the corresponding amino compound of formula I in which $R^3$ is $CH_2NR^4R^5$ wherein $R^4$ is as defined herein and $R^5$ is lower alkyl.

Another aspect of this invention includes compounds of formula IV which are useful intermediates for preparing the compounds of formula I.

The compounds of formula I in which $R^3$ is COOH are useful for treating inflammatory conditions in mammals and the compounds of formula I in which $R^3$ is $CH_2NR^4R^5$ in which $R^4$ and $R^5$ are as defined herein are useful for treating depression in mammals. Pharmaceutical compositions of these compounds are included as one aspect of this invention.

DETAILED DESCRIPTION OF THE INVENTION

The term "lower alkyl" as used herein contemplates both straight and branched chain alkyl radicals containing from one to six carbon atoms and includes methyl, ethyl, propyl, isopropyl, butyl, isobutyl, 2-methylpentyl and the like.

Where the term "lower" is used herein as part of the description of alkylamino and dialkylamino, it contemplates one to six carbon atoms for each alkyl of such a radical and includes methylamino, n-hexylamino, dimethylamino, diethylamino and the like.

The term "lower alkoxy" as used herein contemplates both straight and branched chain alkoxy radicals containing from one to four carbon atoms and includes methoxy, ethoxy, isopropoxy, butoxy and the like.

The term "lower alkanoic acid" as used herein contemplates both straight and branched chain alkanoic acids containing from two to four carbon atoms and includes acetic, propionic and isobutyric acid and the like.

The terms "halogen" and "halo" as used herein include fluorine, chlorine, bromine and iodine, unless stated otherwise.

The 4H-pyrano[4,3-d]thiazole derivatives of formula I in which $R^3$ is COOH form addition salts with suitable inorganic and organic bases. These salts possess the same activities as the parent acid compound when administered to mammals and may be utilized in the same manner. Suitable inorganic bases to form these salts include, for example, the hydroxides, lower alkoxides, carbonates and bicarbonates of sodium, potassium, calcium and magnesium.

Suitable organic bases include the following amines; lower mono-, di- and trialkylamines, the alkyl radicals of which contain up to three carbon atoms, such as methylamine, dimethylamine, triethylamine, ethylamine, di- and triethylamine, methylethylamine; mono-, di- and trialkanolamines, the alkanol radicals of which contain up to three carbon atoms, such as mono-, di- and triethanolanine; alkylenediamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methylmorpholine and N-(2-hydroxyethyl)piperidine, as well as pyridine. Furthermore, there may be mentioned the corresponding quaternary salts, such as the tetraalkyl (for example tetramethyl), alkyl-alkanol (for example methyl-trimethanol and trimethyl-monoethanol) and cyclic ammonium salts, for example the N-methylpyridinium, N-methyl-N-(2-hydroxyethyl)morpholinium, N,N-dimethylmorpholinium, N-methyl-N-(2-hydroxyethyl)morpholinium, N,N-dimethylpiperidinium salts, which are characterized by having good water-solubility. The addition salts thus obtained are the functional equivalents of the parent acid compound in respect to their therapeutic use. Hence, these addition salts are included within the scope of this invention and are limited only by the requirement that the bases employed in forming the salts be pharmaceutically acceptable.

Also included within the scope of this invention are the isomers of the compounds of formula I resulting from the asymmetric centers contained therein.

The 4H-pyrano[4,3-d]thiazole derivatives of formula I in which $R^3$ is $CH_2NR^4R^5$ form addition salts with suitable inorganic and organic acids. These salts possess the same activities as the parent base compound when administered to mammals and may be utilized in the same manner. Suitable acids to form these salts include, for example the common mineral acids, hydrohalic, sulfuric or phosphoric, as well as the organic acids, formic, acetic, maleic, malic, citric, or tartaric acid, or acids which are sparingly soluble in body fluids and which impart slow-release properties to their respective salts such as pamoic or tannic acid. The addition salts thus obtained are the functional equivalent of the parent base compound in respect to their therapeutic use. Hence, these addition salts are included within the scope of this invention and are limited only by the requirement that the acids employed in forming the salts be pharmaceutically acceptable.

ANTI-INFLAMMATORY ACTIVITY

The useful anti-inflammatory effect of the compounds of formula I in which $R^3$ is COOH is demonstrated in standard pharmacological tests, for example, in tests described by R. A. Turner in "Screening Methods in Pharmacology", Academic Press, New York and London, 1965, pp. 152–163.

More particularly exemplified the anti-inflammatory effect for the compounds of this invention is demonstrated in a modification of the established arthritis test described by B. B. Newbould, Br. J. Pharmac:, 35, 487 (1969). In this test rats are made arthritic by treating them with an injection of Freud's adjuvant into the left hind paw. After 14 days (day zero of test) a chronic arthritis is established. At this point the rats are treated with a uniform daily dose of the test compound from day zero to day eight of the test. Results are expressed as the change in volume of the injected paw from day zero. Untreated arthritic rats show an increased paw size whereas active compounds cause a reduction in the volume of the injected paw, both being measured by weighing the amounts of mercury displaced by said paw.

Typical results obtained for the preferred compounds of the present invention in the aforementioned test are as follows.

| Compound | Daily Dose (mg/kg/ p.o.) | Reduction of Paw Size (g of Hg) |
|---|---|---|
| 6,7-dihydro-4-methyl-2-(4-chloro phenyl)-4H-pyrano[4,3-d]thiazole-4-acetic acid (Example 3) | 50 | 8 |
| 6,7-dihydro-4-methyl-2-phenyl-4H-pyrano[4,3-d]thiazole-4-acetic acid (Example 3) | 100 | 5 |
| 6,7-dihydro-4-ethyl-2-(4-chloro-phenyl)-4H-pyrano[4,3-d]thiazole-4-acetic acid (Example 2) | 50 | 4 |
| 6,7-dihydro-4-ethyl-2-phenyl-4H-pyrano[4,3-d]thiazole-4-acetic acid (Example 2) | 100 | 4 |

When the compounds of this invention are employed as anti-inflammatory agents in mammals, e.g. rats, an anti-inflammatory effective amount of the compound is administered, preferably orally, to the mammal, either alone or combined with pharmaceutically acceptable excipients in a dosage form, i.e. capsule or tablet, or they are administered orally in the form of solutions or suspensions.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets may be uncoated or they may be coated by known techniques so as to delay disintegration and absorption in the gastrointestinal tract and thereby provide a sustained action over a longer period.

The aqueous suspensions of the invention contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions may also contain one or more preservatives, one or more coloring agents, one or more flavouring agents and one or more sweetening agents.

Non-aqueous suspensions may be formulated by suspending the active ingredient in a vegatable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions may also contain a sweetening agent, flavouring agent and an anti-oxidant.

The dosage of the compounds of this invention will vary with the particular compound chosen and with the form of administration. Furthermore, it will vary with the particular host under treatment. Generally, the compounds of this invention are administered at a dose level that affords desirable effects without any deleterious side effects. These anti-inflammatorily effective dose levels are usually obtained by oral administration within a therapeutic range of 1.0 mg to 500 mg/kg per day, with a preferred range of 10 to 200 mg/kg per day.

The compounds of this invention possess another useful pharmacologic property; that is the compounds of formula I in which $R^3$ is $CH_2NR^4R^5$ are useful antidepressant agents. The useful antidepressant activity of the compounds of formula I in which $R^3$ is $CH_2NR^4R^5$ and of their acid addition salts with pharmaceutically acceptable acids is demonstrated in standard pharmacologic tests, such as, for example, the tests described by F. Hoflinger and V. Burckhart in "Psychopharmacological Agents", M. Gordon, Ed. Academic Press, New York and London, 1964, pp. 75–83. More specifically, as noted in the latter reference the antidepressant properties of a compound may be demonstrated by its capacity to antagonize the effects of reserpine. Furthermore, it is well documented that reserpine produces in animals a model depression which can be used for detecting antidepressant properties. Accordingly, the compounds of the present invention antagonize reserpine effects in mice at doses ranging from about 5 to 100 mg/kg. For instance, the preferred compound, 4-(3-aminopropyl)-6,7-dihydro-4-methyl-2-phenyl-4H-pyrano[4,3-d]thiazole (Example 35) antagonizes the effects of reserpine in mice, by parenteral administration at doses ranging from about 10 to 30 mg/kg.

When the compounds of this invention are used as antidepressants in mammals, they are formulated and administered orally in the same manner as described above for their use as anti-inflammatory agents. For parenteral administration they may be used in the form of a sterile solution containing other solutes, for example, enough saline or glucose to make the solution isotonic.

PROCESSES

The requisite starting materials for the process for preparing the compounds of formula I are the compounds of formula II and the ketonic compounds of formula III.

The starting materials of formula II in which $R^1$ is as defined herein are either known, for example 2-(4-chlorophenyl)-4-(2-hydroxyethyl)thiazole, described in the U.S. Pat. No. 3,652,575, Mar. 28, 1972, or they may be obtained by the following process:

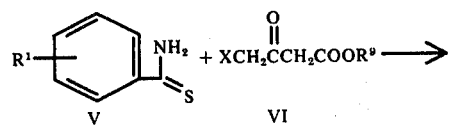

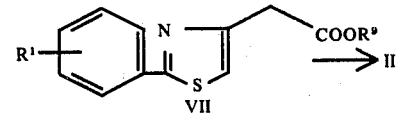

With reference to this process the thiobenzamides of formula V in which $R^1$ is as defined in the first instance and the haloacetoacetates of formula VI in which X is halogen selected from bromine or chlorine and $R^9$ is lower alkyl are reacted together according to the conditions described by S.-I. Kaneko, U.S. Pat. No. 3,705,153, Dec. 5, 1972 to form the phenylthiazolyl acetates of formula VII in which $R^1$ and $R^9$ have the same meaning as described above. The appropriate compound of formula VII is converted to the corresponding starting material of formula II by lithium aluminum hydride reduction (N. G. Gaylord, "Reduction with Complex Metal Hydrides", Interscience Publishers, Inc., New York, 1956, pp. 322–370).

The thiobenzamides of formula V are either known or may be prepared according to known methods. A convenient method involves the treatment of the appropriate benzonitrile with hydrogen sulfide in the presence of ammonia to give the corresponding thiobenzamide, for example, see G. Heymann, Ber. 24, 786 (1891) and A. Silberg et al., Ber. 94, 2887 (1961).

The haloacetoacetates of formula VI are either known or may be prepared according to known methods, for example, see A. Burger and G. E. Ullyot, J. Org. Chem. 12, 342 (1947).

The starting materials of formula III are described below with reference to their specific use in the present process.

The first step of the process for preparing compounds of formula I is the condensation of the compound of formula II with the compound of formula III in the presence of a suitable acid catalyst to give the corresponding compound of formula IV:

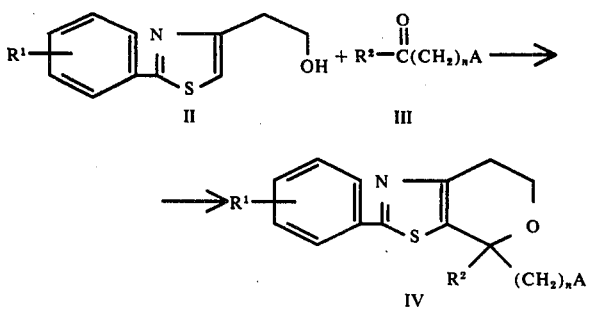

in which $R^1$, $R^2$, A and n are as defined herein.

When practising this condensation an inert organic solvent is generally used as a reaction medium. Any solvent inert to the reaction conditions may be used. Suitable solvents include benzene, toluene, diethyl ether, dioxane, tetrahydrofuran, methylene dichloride, and carbon tetrachloride. Benzene and toluene are especially convenient and practical for this use. However, note that the solvent may be omitted without detrimental effects on the reaction if the reactants are heated to a melt with stirring.

A variety of suitable acid catalysts can be used for this condensation, for example, the type of catalyst used in a Friedel-Crafts reactions, i.e., p-toluenesulfonic acid, aluminum chloride, phosphorus pentoxide, zinc chloride, hydrochloric acid, perchloric acid, trifluoroacetic acid, sulfuric acid, and polyphosphoric acid. See also the list of acid catalysts described by G. A. Olah in "Friedel-Crafts and Related Reactions", Vol. I, G. A. Olah, Ed., Interscience Publishers, New York, N.Y., 1963, pp. 201–366, which includes other suitable proton and Lewis acids. p-Toluenesulfonic acid and polyphosphoric acid are included among the preferred acid catalysts. The amount of acid catalyst used is not especially critical and may range from 0.01 molar equivalents to 100 molar equivalents with respect to the starting material of formula II. A range of from 0.1 to 10 molar equivalents is generally preferred; however, note that the amount of acid catalyst should be in excess of one molar equivalent with respect to the compound of formula III when A is $CH_2NR^4R^5$ as defined herein.

The time of the reaction may range from 10 minutes to 60 hours, with the preferred range being from 1 to 45 hours. The temperature of the reaction may range from 20° to 120° C, preferably 80° to 120° C.

A more detailed description of the preparation of the compounds of formula IV and a description of their subsequent conversion to the compounds of formula I are disclosed below. For convenience these descriptions are categorized into sections according to the group selected for A of the starting material of formula III.

a. Preparation and Conversion of Intermediates of Formula IV (A = $COOR^6$)

Intermediates of formula IV in which A is $COOR^6$ wherein $R^6$ is hydrogen or lower alkyl are readily obtained by the above condensation using ketoacids or ketoesters of formula III in which $R^2$ and n are as defined above, and A is $COOR^6$ as defined above, together with the starting material of formula II. It should be noted that said intermediate in which A is $COOR^6$ wherein $R^6$ is hydrogen is the compound of formula I in which $R^3$ is COOH.

Generally comparable yields of product are obtained in this process when either the ketoacid or the corresponding ketoester is used. However, in the case where it is desired to prepare an acid compound of formula IV in which A is COOH and n is the integer one (i.e., an acetic acid of formula IV), it is preferable to condense the appropriate β-ketoester rather than the corresponding β-ketoacid and then hydrolyze the resulting ester product to give the desired acid compound. Said acid compound is represented by formula IV in which A is $COOR^6$ wherein $R^6$ is hydrogen and n is the integer one or by formula I in which $R^3$ is COOH and n is the integer one.

Moreover, in the general practise of this invention it is often more convenient to prepare the acid compounds either of formula I or of formula IV by using the ketoester instead of the ketoacid in this process and to hydrolyze the resulting ester product to the desired acid, the reason being that the ketoesters are generally more readily available either commercially or by synthesis.

The compounds of this invention, bearing an acid substituent, of formula I in which $R^3$ is COOH and $R^1$, $R^2$ and n are as defined in the first instance, are prepared from their corresponding ester compounds of formula IV by treatment with a hydrolyzing agent. For basic hydrolysis a preferred method involves subjecting the lower alkyl ester to the action of a strong base, for example, sodium or potassium hydroxide, in the presence of sufficient water to effect hydrolysis of the ester. The hydrolysis is performed using a suitable solvent, for example, methanol or ethanol. The reaction mixture is maintained at a temperature of from 20° C to the boiling point of the reaction mixture until hydrolysis occurs. Usually from 1 to 30 hours is sufficient for this hydrolysis. The alkaline reaction mixture is extracted with a substantially water immiscible organic solvent, preferably diethyl ether, and rendered acidic with an acid, for example, hydrochloric or sulfuric acid. The acidic solution is extracted with a substantially water immiscible organic solvent, preferably diethyl ether. The organic extract is evaporated to obtain said corresponding acid of formula I.

From the above described alkaline hydrolysis a by-product resulting from decarboxylation of said acid is obtained. Said by-product is the corresponding compound of formula I in which $R^1$, $R^2$ and n are as defined above and $R^3$ is hydrogen. The latter compound is obtained by evaporating the organic extract of the alkaline aqueous solution.

The β- and γ-ketoacids and -ketoesters of formula III are either known, for example, levulinic acid or ethyl acetoacetate, or they may be prepared by known methods described in general organic chemistry textbooks. For example, a comprehensive review of the properties and preparation of such β- and γ-ketoacids and -ketoesters may be found in "Rodd's Chemistry of the Carbon Compounds", S. Coffey, Ed., Vol. 1d, 2nd ed., Elsevier Publishing Co., Amsterdam, 1965, pp. 226–274.

Thereafter these intermediate acids and esters of formula IV can be converted by amidation followed by reduction to the corresponding amino compounds of formula I in which $R^1$, $R^2$ and n are as defined above and $R^3$ is $CH_2NR^4R^5$ therein $R^4$ and $R^5$ are as defined above.

More specifically, in the case where the acid intermediate of formula IV is employed, said acid is converted to a corresponding activated carbonyl. A convenient activated carbonyl is the corresponding mixed anhydride of said acid. Such a mixed anhydride can be prepared by treating said acid with a lower alkyl chloroformate, preferably ethyl chloroformate, in the presence of triethylamine. Treatment of the activated carbonyl, preferably the mixed anhydride, with an appropriate amine of formula $HNR^4R^5$ in with $R^4$ and $R^5$ are as defined above, for example, ammonia, dimethylamine or butylamine, yields the corresponding amide of formula IV in which A is $CONR^4R^5$.

Alternatively, the latter amides are also obtained by treating the ester intermediates of formula IV with the appropriate amine according to known amidation methods, for example, see A.L.F. Beckwith in "The Chemistry of Amides", J. Zalicky, Ed., Interscience Publishers, New York, 1970, pp. 96–105.

Thereafter, the amides so obtained are reduced with a suitable complex metal hydride to yield the corresponding amino compounds of formula I. Examples of suitable complex metal hydrides are lithium aluminum hydride, lithium aluminum hydride-aluminum chloride, aluminum hydride-aluminum chloride, diborane, or sodium borohydride-aluminum chloride. Lithium aluminum hydride is preferred.

A modification relating to the preceding general reduction of the above amides of formula IV in which A is $CONR^4R^5$ wherein $R^4$ and $R^5$ are as defined above is applicable to the reduction of the tertiary, secondary and primary amides, described herein, and is a preferred modification for the reduction of the latter two. In practising this modification, the aforementioned amide of formula IV is treated with triethyloxonium fluoroborate or dimethyl sulfate, see H. Bredereck, et al., Chem. Ber., 98, 2754 (1965), in an inert solvent, for example methylene dichloride, whereby the corresponding iminoether fluoroborate or methyl sulfate salt is obtained, respectively. Subsequent reduction of the salt thus obtained with a complex metal hydride, similar to the reduction described previously for the amides, yields the corresponding amino compounds of formula I. Alternatively, the above fluoroborate or methyl sulfate salt derived from a secondary or primary amide is decomposed by base treatment, for example, with 10% sodium hydroxide or triethylamine, to give the corresponding iminoether which is then reduced in a like manner to the corresponding amino compound of formula I.

Alternatively, the amino compounds of formula I are also obtained by reducing the above described acid of formula IV to the corresponding alcohol with a suitable complex metal hydride in the manner described above. Lithium aluminum hydride is preferred. Said alcohol is converted to a reactive intermediate such as the corresponding mesylate, tosylate or halide which is reacted with two or more equivalents of an amine of formula $NHR^4R^5$ in which $R^4$ and $R^5$ are as defined in the first instance. In practising this latter process, it is preferable to react said alcohol with a mesylating or tosylating agent, reacting the resulting respective mesylated or tosylated intermediate with a halogenating agent in which the halogen is selected from bromine, chlorine or iodine to obtain the corresponding halogenated intermediate and reacting said halogenated intermediate with an amine of formula $NHR^4R^5$ in which $R^4$ and $R^5$ are as defined herein to give the corresponding amino compound of formula I in which $R^3$ is $CH_2NR^4R^5$. Preferably the latter reaction is performed in a suitable inert solvent, for example, tetrahydrofuran, at 0° to 100° C for a period of 5 to 30 hours.

b. Preparation and Conversion of Intermediates of Formula IV (A = $CONR^4R^5$)

The intermediates of formula IV in which A is $CONR^4R^5$ wherein $R^4$ and $R^5$ are as described above, see also section (a), can be obtained directly by reacting the appropriate starting material of formula II and the appropriate β- or γ-ketoamide of formula (III) in which $R^2$ and $n$ are as defined above and A is $CONR^4R^5$ in which $R^4$ and $R^5$ are as defined above according to the condensation conditions described above. The ketoamides required for this condensation are either known, for example N,N-dimethylacetoacetamide, or they may be prepared by known methods, for instance, see "Rodd's Chemistry of the Carbon Compounds", cited above, Vol. 1d, pp. 226–274.

Thereafter these amides are converted by the process described above in section (a), to the corresponding amino compounds of formula I in which $R^3$ is $CH_2NR^4R^5$ and $R^1$, $R^2$, $R^4$, $R^5$ and $n$ are as defined above.

c. Preparation and Conversion of Intermediates of Formula IV (A = $CH_2OCOR^7$)

Intermediates of formula IV in which A is $CH_2OCOR^7$ wherein $R^7$ is lower alkyl are obtained when a starting material of formula II is condensed with a ketoalcohol lower alkanoic acid ester of formula III in which $R^2$ and $n$ are as defined above and A is $CH_2OCOR^7$ in which $R^7$ is as defined above in the presence of a suitable acid catalyst according to the condensation conditions described above. The ketoalcohol lower alkyl esters are either known, for example, 1-acetoxy-3-butanone, or may be prepared by known methods, for instance, see "Rodd's Chemistry of the Carbon Compounds", cited above Vol. 1d, pp. 49–54.

These intermediates of formula IV are utilized for the preparation of the amino compounds of formula I of this invention in the following manner: The intermediate is hydrolyzed with an aqueous alcoholic solution of a suitable alkali, for example, sodium or potassium hydroxide in aqueous methanol, to afford the corresponding primary alcohol. It should be noted also that the latter primary alcohol is obtained directly by the reduction of the appropriate intermediate acids or intermediate esters of formula IV, as described herein in section (a), using a suitable complex metal hydride as described therein, Thereafter, the above corresponding alcohol is converted, as described in section (a), to the corresponding amino compounds of formula I in which $R^3$ is $CH_2NR^4R^5$ and $R^1$, $R^2$, $R^4$, $R^5$ and $n$ are as defined herein.

If desired the amino compounds of formula I in which $R^3$ is $CH_2NR^4R_5$ wherein both $R^4$ and $R^5$ are hydrogen may be further N-alkylated on the nitrogen of the primary amine with the appropriate lower alkyl halide to the corresponding amino compounds of formula I in which $R^3$ is $CH_2NR^4R^5$ wherein $R^4$ is hydrogen or lower alkyl and $R^5$ is lower alkyl (i.e. secondary or tertiary amines). In this case, depending on the particular derivative desired, the N-alkylation may be effected with one or two moles to the alkyl halide to give respectively the secondary ($R^4$ = H and $R^5$ = lower alkyl) or tertiary amine ($R^4 = R^5$ = lower alkyl). On the other hand the N-alkylation may be effected in two steps introducing a different alkyl group each time to afford the corresponding tertiary amine in which $R^4$ and $R^5$ are different lower alkyls.

When it is desired to prepare the above tertiary amine compounds in which $R^4$ or $R^5$ are either or both methyl, an alternative alkylation method comprises reacting the appropriate corresponding primary or secondary amine with an aqueous mixture of a substantial excess of formaldehyde and formic acid according to the conditions of the Eschweiler-Clarke reaction, see M. L. Moore, Organic Reactions, 5, 301 (1949), whereby N-methylation is effected.

d. Preparation and Conversion of Intermediates of Formula IV (A = $CH_2NR^4COR^8$)

Intermediates of formula IV in which A is $CH_2NR^4COR^8$ wherein $R^4$ is hydrogen or lower alkyl and $R^8$ is hydrogen or an alkyl containing one to five carbon atoms are readily obtained by the above condensation by using ketoamides of formula III in which $R^2$ and $n$ are as defined above and A is $CH_2NR^4COR^8$ wherein $R^4$ and $R^8$ are as defined above together with the appropriate starting material of formula II.

The ketoamides used herein are either known, for example, 1-acetamido-3-butanone, or may be prepared by known procedures, for example, see "Methoden der Organischen Chemie", Houben-Weyl, E. Muller, Ed., Vol XI/I, Georg Thieme Varlag, Stuttgart, 1957, pp. 58–62, 285–289 and 508–590, and F. F. Blicke, Organic Reactions, I, 303 (1942).

Thereafter, reduction with a complex metal hydride, described in section (a), converts the instant intermediates to the corresponding amino compounds of formula I in which $R^3$ is $CH_2NR^4R^5$, $R^1$, $R^2$, $R^4$ and $n$ are as defined herein and $R^5$ is lower alkyl.

e. Preparation of Compounds of Formula IV (A = $CH_2NR^4R^5$) = Compounds of Formula I The starting materials of formula II in which $R^1$ is as defined above are condensed in the presence of an acid catalyst with an aminoketone of formula III in which $R^2$ and $n$ are as defined above and A is $CH_2NR^4R^5$ wherein $R^4$ and $R^5$ are as defined herein to give directly the amino compounds of formula I.

The requisite aminoketones for this reaction are either known, for example, 1-dimethylamino-3-butanone, 1-methylamino-3-pentanone, see F. F. Blicke, cited above, or they may be prepared by known procedures, for example, see "Methoden der Organischen Chemie", cited above, Vol. XI/I, 1957, pp. 58–62, 258–289 and 508–509.

In practising this present condensation it is generally advantageous to utilize substantially equimolar amounts of the starting material of formula II and the aminoketone in the presence of an acid catalyst. In this particular condensation the amount of the aforementioned acid catalyst employed, ranges generally from about 1.01 to 100 molar equivalents with respect to the amount of aminoketone reactant, a range of from 1.05 to 10 molar equivalents being preferred. Optionally, one may employ the acid addition salts of the aforementioned aminoketones, for example the hydrochloride or the sulfate salt. In this case the amount of acid catalyst, for example p-toluenesulfonic acid, may range from 0.01 to 100 molar equivalents. The reaction is performed conveniently and advantageously in an inert organic solvent, for example, toluene, o-xylene or isobutyl ether. Reaction time and temperature depends on the particular reactants employed and may be varied. The most convenient reaction time is from one-half to 48 hours, preferably one-half to eight hours, and reaction temperatures from 20° to 110° C, preferably 80° to 110° C.

The following examples illustrate further this invention.

EXAMPLE 1

2-Phenyl-4-(β-hydroxyethyl)thiazole (11; $R^1$ = H)

Ethyl γ-bromoacetoacetate [2.62 g, 0.9–1.0 mole, described by A. Burger and G. E. Ullyot. J. Org. Chem., 12, 346 (1947)] is added in one portion to a suspension of thiobenzamide [117.5 g, 0.857 mole, described by A. Silberg et al., Ber., 94, 2887 (1961)] in ethanol. The clear solution is refluxed on a steam bath for 2 hr, cooled and slowly added with stirring to ether (3500 ml). The white crystalline precipitate is collected, washed with ether and partitioned between water and ether. Sodium bicarbonate is added in portions until the mixture is alkaline. The mixture is extracted with ether, the ether solution is washed with saturated sodium chloride solution, dried, and evaporated to give ethyl 2-phenylthiazole-4-acetate (VII; $R^1$ = H, $R^9$ = $CH_2CH_3$), $\gamma_{max}^{CHCl_3}$ 1725 cm$^{-1}$.

Reduction of the latter ester to the title compound is effected as follows: The ester (159 g) is dissolved in dry tetrahydrofuran (250 ml) and added dropwise during 30 min to a stirred mixture of lithium aluminum hydride (50 g) in tetrahydrofuran. The mixture is stirred for 1 hour, cooled and water (150 ml) is slowly added. The mixture is dried over magnesium sulfate and evaporated to give the title compound as a yellow oil, $\gamma_{max}^{CHCl_3}$ 3610, 3420 and 1520 cm$^{-1}$.

By following the procedure of this example and using the appropriate substituted thiobenzamides of formula V then other substituted 4-(β-hydroxyethyl)thiazoles of formula II, for example, those described as starting materials in Examples 4 to 14, are obtained. More specifically exemplified, the replacement of thiobenzamide with an equivalent amount of p-chlorthiobenzamide gives 2-(p-chlorophenyl)-4-(β-hydroxyethyl)thiazole, (11, $R^1$ = Cl), mp 60°–61.5° C (lit. mp 66°–66.5° C as reported in the above cited U.S. Pat. No. 3,652,575).

EXAMPLE 2

6,7-Dihydro-4-ethyl-2-phenyl-4H-pyrano[4,3-d]thiazole-4-acetic acid (1; $R^1 = R^2 = CH_2CH_3$, $R^3 =$ COOH and $n = 1$)

a. A mixture of the starting material of formula II, 2-phenyl-4-(β-hydroxyethyl)thiazole (30.8 g, 0.15 mole, described in Example 1), ethyl propionylacetate (28.8 g, 0.2 mole) and p-toluene-sulfonic acid hydrate (0.25 mole) in toluene (1200 ml) is heated at reflux temperature, with water separation, for 17 hr. Additional ethyl propionylacetate (6 g) and p-toluenesulfonic acid hydrate is added and refluxing is continued for 24 hr. The mixture is evaporated under reduced pressure and the residue is triturated with petroleum ether. The residue is dissolved in a mixture of aqueous sodium bicarbonate solution and ether. The organic solution is separated, dried over sodium sulfate and evaporated under reduced pressure to give ethyl 6,7-dihydro-4-ethyl-2-phenyl-4H-pyrano[4,3-d]thiazole-4- acetate (IV, $R^1$ = H, $R^2$ = $CH_2CH_3$, A = $COOCH_2CH_3$ and $n$ = 1).

b. Hydrolysis of the latter ester to the title compound is effected as follows: The ester is dissolved in 500 ml of 3% methanolic sodium hydroxide and the solution refluxed for 4 hr. The solvent is evaporated, water is added and the solution is extracted with ether. The organic extract is retained. The aqueous phase is acidified with 10% hydrochloric acid, and extracted with ether. The organic phase is washed with saturated sodium chloride solution, dried over sodium sulfate and evaporated to dryness. Crystallization of the residue from chloroform-ether-pentane gives the title compound, mp 106°–108° C, $\gamma_{max}^{CHCl_3}$ 2900 and 1715 cm$^{-1}$. The ether extract obtained from the alkaline aqueous solution is subjected to chromatography on silica gel. Elution with benzene-ethyl acetate (9:1) and evaporation of the eluate gives an oil which on trituration with ether containing hydrogen chloride yields the by-products, 6,7-dihydro-4-methyl-4-ethyl-2-phenyl-4H-pyrano[4,3-d]thiazole hydrochloride.

In the same manner but replacing 2-phenyl-4-($\beta$-hydroxyethyl)-thiazole with an equivalent amount of 2-(4-chlorophenyl)-4-($\beta$-hydroxyethyl)thiazole the intermediate ester, ethyl 6,7-dihydro-4-ethyl-2-(4-chlorphenyl)-4H-pyrano[4,3-d]thiazole-4-acetate (IV, $R^1$ = Cl, $R^2$ = $CH_2CH_3$, A = $COOCH_2CH_3$ and $n$ = 1) is obtained. Alkaline hydrolysis of the latter ester gives 6,7-dihydro-4-ethyl-2-(4-chlorophenyl)-4H-pyrano[4,3-d]thiazole-4-acetic acid (I; $R^1$ = Cl, $R^2$ = $CH_2CH_3$, $R^3$ = COOH and $n$ = 1), mp 190°–191° C, after crystallization from methanol. The ether extract obtained from the alkaline aqueous solution is purified to give the by-products 6,7-dihydro-4-ethyl-4-methyl-2-(4-chlorophenyl)-4H-pyrano[4,3-d]thiazole hydrochloride, mp 153°–154° C, after trituration with ether containing hydrogen chloride.

In the same manner but replacing p-toluenesulfonic acid, with phosphorus pentoxide, hydrochloric acid or polyphosphoric acid, the title compound is also obtained.

EXAMPLE 3

6,7-Dihydro-4-methyl-2-(4-chlorophenyl)-4H-pyrano[4,3-d]thiazole-4-acetic acid (1; $R^1$ = Cl, $R^2$ = $CH_3$, $R^3$ = COOH and $n$ = 1)

A mixture of the starting material of formula II, 2-(4-chlorophenyl)-4-($\beta$-hydroxyethyl)thiazole (24.0 g, 0.1 mole, described in Example 1), ethyl acetoacetate (19.5 g, 0.15 mole) and p-toluenesulfonic acid hydrate (38.0 g, 0.2 mole) in toluene (1000 ml) is heated at reflux temperature, with water separation, for 20 hr. The mixture is evaporated under reduced pressure and the residue is triturated with petroleum ether. The residue is dissolved in a mixture of aqueous sodium bicarbonate solution and ether. The organic solution is separated, washed with saturated sodium chloride solution, dried over sodium sulfate and evaporated under reduced pressure to give ethyl 6,7-dihydro-4-methyl-2-(4-chlorphenyl)-4H-pyrano[4,3-d]thiazole-4-acetate (IV, $R^1$ = Cl, $R^2$ = $CH_3$, A = $COOCH_2CH_3$ and $n$ = 1).

The latter ester is dissolved in methanol (500 ml) followed by the addition of sodium hydroxide (80 g) and the resulting mixture is heated at reflux temperature for 5 hr. The solvent is removed by distillation, water is added to the residue and the solution is extracted with ether. The aqueous basic phase is mixed with ether and the mixture is acidified with dilute hydrochloric acid. The organic phase is separated, washed with saturated sodium chloride solution, dried over sodium sulfate, and evaporated under reduced pressure. The residue is crystallized from chloroform-ether to give the title compound; mp 162°–164° C, $\gamma_{max}^{CHCl}$ 2900 and 1705 cm$^{-1}$.

The ether extract obtained from the alkaline aqueous solution is subjected to chromatography on silica gel. Elution with benzene-ethyl acetate (9:1), evaporation of the eluate and crystallization from n-pentane gives the by-product, 6,7-dihydro-4,4-dimethyl-2-(4-chlorophenyl)-4H-pyrano[4,3-d]thiazole.

In the same manner but replacing 2-(4-chlorphenyl)-4-($\beta$-hydroxyethyl)thiazole with an equivalent amount of 2-phenyl-4-($\beta$-hydroxethyl)thiazole the intermediate ester, ethyl 6,7-dihydro-4-methyl-2-phenyl-4H-pyrano[4,3-d]thiazole acetate (IV; $R^1$ = H, $R^2$ = $CH_3$, A = $COOCH_2CH_3$ and $n$ = 1), $\gamma_{max}^{CHCl_3}$ 1730 cm$^{-1}$, is obtained. Alkaline hydrolysis of the latter ester gives 6,7-dihydro-4-methyl-2-phenyl-4H-pyrano[4,3-d]thiazole-4-acetic acid (1, $R^1$ = H, $R^2$ = $CH_3$ $R^3$ = COOH and $n$ = 1), mp 143°–145° C, after crystallization from ether-hexane. The ether extract obtained from the alkaline aqueous solution is purified to give the by-product, 6,7-dihydro-4,4-dimethyl-2-phenyl-4H-pyrano[4,3-d]thiazole, mp 65°–66° C, after crystallization from n-pentane.

In the same manner but replacing ethyl acetoacetate with an equivalent amount of methyl acetoacetate the title compound is also obtained.

The procedures of Examples 2 and 3 are followed to prepare other compounds of formula I in which $R^3$ is COOH and $R^1$, $R^2$ and $n$ are as defined herein. Examples of such compounds are listed in Table I. In each of these examples the appropriate starting materials of formula II and formula III (A = COOR$^6$) are listed together for the preparation of the corresponding acid of formula I in which $R^3$ is COOH.

TABLE 1

| | STARTING MATERIAL FORMULA II | | STARTING MATERIAL OF FORMULA III | | | PRODUCT: (PREFIX LISTED BELOW) -4H-PYRANO[4,3-d]THIAZOLE-4- (SUFFIX LISTED BELOW) |
|---|---|---|---|---|---|---|
| Ex. | $R^1$ | $R^2$ | n | A | | Prefix//Suffix |
| 4 | H | $CH_3$ | 2 | $COOC_2H_5$ | | 6,7-dihydro-4-methyl-2-phenyl//propionic acid, mp 148 – 150° C |
| 5 | H | n-$C_3H_7$ | 1 | $COOC_2H_5$ | | 6,7-dihydro-4-(n-propyl)-2-phenyl//acetic acid, $\gamma_{max}^{CHCl_3}$ 2900, 1710 and 1540 cm$^{-1}$ |
| 6 | 3-Br | $CH_3$ | 2 | $COOCH_3$ | | 6,7-dihydro-4-methyl-2-(3-bromophenyl)//propionic acid |
| 7 | 2-I | $C_2H_5$ | 1 | $COOCH_3$ | | 6,7-dihydro-4-ethyl-2-(2-iodophenyl)//acetic acid |

TABLE 1-continued

| Ex. | STARTING MATERIAL FORMULA II R$^1$ | STARTING MATERIAL OF FORMULA III R$^2$ | n | A | PRODUCT: (PREFIX LISTED BELOW) -4H-PYRANO[4,3-d]THIAZOLE-4- (SUFFIX LISTED BELOW) Prefix//Suffix |
|---|---|---|---|---|---|
| 8 | 3-NO$_2$ | n-C$_5$H$_{11}$ | 1 | COOCH$_3$ | 6,7-dihydro-4-(n-pentyl)-2-(3-nitrophenyl)//acetic acid |
| 9 | 1-CH$_3$ | n-C$_4$H$_9$ | 2 | COOCH$_3$ | 6,7-dihydro-4-(n-butyl)-2-(1-methylphenyl)//propionic acid |
| 10 | 3-CH$_3$O | i-C$_3$H$_7$ | 2 | COOC$_2$H$_5$ | 6,7-dihydro-4-(isopropyl)-2-(3-methoxyphenyl)//-propionic acid |
| 11 | 4-n-C$_3$H$_7$O | C$_2$H$_5$ | 1 | COOCH$_3$ | 6,7-dihydro-4-ethyl-2-(4-n-propoxyphenyl)//-acetic acid |
| 12 | 4-i-C$_4$H$_9$O | CH$_3$ | 2 | COOCH$_3$ | 6,7-dihydro-4-methyl-2-(4-isobutoxyphenyl)//-propionic acid |
| 13 | 2-NO$_2$ | i-C$_6$H$_{13}$ | 1 | COOCH$_3$ | 6,7-dihydro-4-(isohexyl)-2-(2-nitrophenyl)//acetic acid |
| 14 | 4-n-C$_5$H$_{11}$ | i-C$_4$H$_9$ | 2 | COOCH$_3$ | 6,7-dihydro-4-(isobutyl)-2-(4-n-pentylphenyl)//-propionic acid |

EXAMPLE 15

N,N-Dimethyl-6,7-dihydro-4-methyl-2-phenyl-4H-pyrano[4,3-d]thiazole-4-acetamide (IV; R$^1$ = H, R$^2$ = CH$_3$, A = CON(CH$_3$)$_2$ and $n$ = 1)

To a stirred solution of 6,7-dihydro-4-methyl-2-phenyl-4H-pyrano[4,3-d]thiazole-4-acetic acid (10 g, 34.6 mmoles, described in Example 3) in dry tetrahydrofuran (150 ml), cooled to −5° C, is added triethylamine (10 ml, 70 mmoles), followed by ethyl chlorformate (4.16 ml, 52 mmoles). After stirring for 2.5 hours at 0° C, a solution of 40% aqueous dimethylamine (50 ml) is added. The mixture is stirred at room temperature for 1 hour and evaporated under reduced pressure. The residue is dissolved in a mixture of chloroform-water. The organic phase is separated, washed with aqueous sodium bicarbonate solution, water, dried over sodium sulfate, treated with charcoal and evaporated to give the title compound as an oil, $\gamma_{max}^{CHCl_3}$ 1640 cm$^{-1}$.

In the same manner but replacing the 40% aqueous solution of dimethylamine with an equivalent amount of one of the amines of formula HNR$^4$R$^5$, ammonium hydroxide (concentrated), methylamine (40% aqueous solution), diethylamine (30% aqueous solution) and isopropylamine (40% aqueous solution), 6,7-dihydro-4-methyl-2-phenyl-4H-pyrano[4,3-d]thiazole-4-acetamide, N-methyl-6,7-dihydro-4-methyl-2-phenyl-4H-pyrano[4,3-d]thiazole-4-acetamide, N,N-diethyl-6,7-dihydro-4-methyl-2-phenyl-4H-pyrano[4,3-d]thiazole-4-acetamide and N-isopropyl-6,7-dihydro-4-methyl-2-phenyl-4H -pyrano[4,3-d]thiazole-4-acetamide are obtained respectively.

The procedure of Example 15 is followed to prepare other amides of formula IV in which R$^1$, R$^2$ and n are as defined herein and A is CONR$^4$R$^5$ in which R$^4$ and R$^5$ are as defined herein. Examples of such amides are listed in Table 2.

In each of these Examples the appropriate starting material of formula I (R$^3$ = COOH) is listed together with the amine used for the preparation of the amide, each starting material being noted by the Example in which it is prepared.

TABLE 2

| EX. | NO. OF EXAMPLE IN WHICH STARTING MATERIAL IS PREPARED | AMINE | PRODUCT: (PREFIX LISTED BELOW) -4H-PYRANO[4,3-d]THIAZOLE-4- (SUFFIX LISTED BELOW) Prefix//Suffix |
|---|---|---|---|
| 16 | 2 | i-C$_3$H$_7$NH$_2$ | N-isopropyl-6,7-dihydro-4-ethyl-2-phenyl//acetamide |
| 17 | 2 | (C$_2$H$_5$)$_2$NH | N,N-diethyl-6,7-dihydro-4-ethyl-2-phenyl//acetamide |
| 18 | 3 | NH$_3$ | 6,7-dihydro-4-methyl-2-(4-chlorophenyl)//acetamide |
| 19 | 4 | NH$_3$ | 6,7-dihydro-4-methyl-2-phenyl//propionamide, nmr (CDCl$_3$) δ1.58 (s, 3H), 2.9 (m, 2H), 4.08 (m, 2H), 5.85 (s, 2H) and 7.3 − 8.05 (m, 5H) |
| 20 | 4 | (CH$_3$)$_2$NH | N,N-dimethyl-6,7-dihydro-4-methyl-2-phenyl//propionamide, $\Gamma_{max}^{CHCl_3}$ 1640 and 698 cm$^{-1}$ |
| 21 | 5 | i-C$_3$H$_7$NH$_2$ | N-isopropyl-6,7-dihydro-4-(n-propyl)-2-phenyl//acetamide |
| 22 | 6 | n-C$_6$H$_{13}$NH$_2$ | N-(n-hexyl)-6,7-dihydro-4-methyl-2-(3-bromophenyl)//-propionamide |
| 23 | 7 | (CH$_3$)$_2$NH | N,N-dimethyl-6,7-dihydro-4-ethyl-2-(2-iodophenyl)//-acetamide |
| 24 | 8 | NH$_3$ | 6,7-dihydro-4-(n-pentyl)-2-(3-nitrophenyl)//acetamide |
| 25 | 9 | (C$_2$H$_5$)$_2$NH | N,N-diethyl-6,7-dihydro-4-(n-butyl)-2-(1-methylphenyl)//-propionamide |

TABLE 2-continued

| EX. | NO. OF EXAMPLE IN WHICH STARTING MATERIAL IS PREPARED | AMINE | PRODUCT: (PREFIX LISTED BELOW) -4H-PYRANO[4,3-d]THIAZOLE-4- (SUFFIX LISTED BELOW) Prefix//Suffix |
|---|---|---|---|
| 26 | 10 | n-$C_4H_9NH_2$ | N-(n-butyl)-6,7-dihydro-4-isopropyl-2-(3-methoxyphenyl)//propionamide |
| 27 | 11 | (n-$C_3H_7)_2$NH | N,N-di(n-propyl)-6,7-dihydro-4-ethyl-2-(4-n-propoxyphenyl)//acetamide |
| 28 | 12 | i-$C_5H_{11}NH_2$ | N-isopentyl-6,7-dihydro-4-methyl-2-(4-isobutoxyphenyl)//propionamide |
| 29 | 13 | $CH_3NH_2$ | N-methyl-6,7-dihydro-4-isohexyl-2-(2-nitrophenyl)//acetamide |
| 30 | 14 | $C_2H_5NH_2$ | N-ethyl-6,7-dihydro-4-isobutyl-2-(4-n-pentylphenyl)//propionamide |

EXAMPLE 31

4-[2-(Dimethylamino)ethyl]-6,7-dihydro-4-methyl-2-phenyl-4H-pyrano[4,3-d]-thiazole (I; $R^1$ = H, $R^2$ = $CH_3$, $R^3$ = $N(CH_3)_2$ and $n$ = 1)

A solution of the amide of formula IV, N,N-dimethyl-6,7-dihydro-4-methyl-2-phenyl-4H-pyrano[4,3-d]thiazole-4-acetamide (0.650 g, 2.06 mmoles, described in Example 15), in tetrahydrofuran (20 ml) is added to a cold (0° C) solution of lithium aluminum hydride (0.157 g, 4.12 mmoles) in tetrahydrofuran. The mixture is stirred at room temperature for 1 hour and water is added. The mixture is dried over magnesium sulfate and evaporated under reduced pressure.

The residue is subjected to chromatography on silica gel. Elution with chloroform-methanol (9:1) and evaporation of the eluate gives the title compound, nmr ($CDCl_3$) δ 1.55 (s, 3H), 2.25 (s, 6H), 1.9–2.6 (m, 4H), 2.9 (t, J = 5.5 Hz, 2H), 4.05 (t. J = 5.5 Hz, 2H) and 7.25–8.05 (m, 5H).

The corresponding hydrobromic acid addition salt (hydrobromide) of the title compound has mp 237°–238° C, after crystallization from chloroform-methanol-ether.

In the same manner but replacing lithium aluminum hydride with an equivalent amount of lithium aluminum hydride-aluminum chloride, aluminum hydride-aluminum chloride, diborane, or sodium borohydride-aluminum chloride, the title compound is also obtained.

In the same manner but replacing N,N-dimethyl-6,7-dihydro-4-methyl-2-phenyl-4H-pyrano[4,3-d]thiazole-4-acetamide with an equivalent amount of the following amides described in Example 15, 6,7-dihydro-4-methyl-2-phenyl-4H-pyrano[4,3-d]thiazole-4-acetamide, N-methyl-6,7-dihydro-4-methyl-2-phenyl[4,3-d]thiazole-4-acetamide, N,N-diethyl-6,7-dihydro-4-methyl-2-phenyl-4H-pyrano[4,3-d]thiazole-4-acetamide and N-isopropyl-6,7-dihydro-4-methyl-2-phenyl-4H-pyrano[4,3-d]thiazole-4-acetamide, there are obtained, 4-(2-aminoethyl)-6,7-dihydro-4-methyl-2-phenyl-4H-pyrano[4,3-d]thiazole, 4-[2-(methylamino)ethyl]-6,7-dihydro-4-methyl-2-phenyl[4,3-d]thiazole, 4-[2-(diethylamino)ethyl]-6,7-dihydro-4-methyl-2-phenyl-4H-pyrano[4,3-d]thiazole and 4-[2-(isopropylamino)ethyl]-6,7-dihydro-4-methyl-2-phenyl-4H-pyrano[4,3-d]-thiazole, respectively.

By following the procedure of Example 31 but using as starting material an equivalent amount of one of the amide compounds of formula IV described in Examples 16 to 30 the corresponding amino compounds of formula I are obtained. Examples of such compounds of formula I are listed as products in Table 3 together with the appropriate starting material. In each case the starting material is noted by the example in which it is prepared.

TABLE 3

| EX. | NO. OF EXAMPLE IN WHICH STARTING MATERIAL IS PREPARED | PRODUCT: (PREFIX LISTED BELOW) -4H-PYRANO[4,3-d]THIAZOLE |
|---|---|---|
| 32 | 16 | 4-[2-(isopropylamino)ethyl]-6,7-dihydro-4-ethyl-2-phenyl |
| 33 | 17 | 4-[2-(diethylamino)ethyl]-6,7-dihydro-4-ethyl-2-phenyl |
| 34 | 18 | 4-(2-aminoethyl)-6,7-dihydro-4-methyl-2-(4-chlorophenyl) |
| 35 | 19 | 4-(3-aminopropyl)-6,7-dihydro-4-methyl-2-phenyl, dihydrobromide mp 193 – 195° C |
| 36 | 20 | 4-[3-(dimethylamino)propyl]-6,7-dihydro-4-methyl-2-phenyl, dihydrobromide mp 212 – 213° C |
| 37 | 21 | 4-[2-(isopropylamino)ethyl]-6,7-dihydro-4-(n-propyl)-2-phenyl |
| 38 | 22 | 4-[3-(n-hexylamino)propyl]-6,7-dihydro-4-methyl-2-(3-bromophenyl) |
| 39 | 23 | 4-[2-(dimethylamino)ethyl]-6,7-dihydro-4-ethyl-2(2-iodophenyl) |
| 40 | 24 | 4-(2-aminoethyl)-6,7-dihydro-4-(n-pentyl)-2-(3-nitrophenyl) |
| 41 | 25 | 4-[3-(diethylamino)propyl]-6,7-dihydro-4-(n-butyl)-2-(1-methylphenyl) |
| 42 | 26 | 4-[3-(n-butylamino)propyl]-6,7-dihydro-4-isopropyl-2-(3-methoxyphenyl) |
| 43 | 27 | 4-[2-(di-n-propylamino)ethyl]-6,7-dihydro-4-ethyl-2-(4-n-propoxyphenyl) |

TABLE 3-continued

| EX. | NO. OF EXAMPLE IN WHICH STARTING MATERIAL IS PREPARED | PRODUCT: (PREFIX LISTED BELOW) -4H-PYRANO[4,3-d]THIAZOLE |
|---|---|---|
| 44 | 28 | 4-[3-(isopentylamino)propyl]-6,7-dihydro-4-methyl-2-(4-isobutoxyphenyl) |
| 45 | 29 | 4-[2-(methylamino)ethyl]-6,7-dihydro-4-isohexyl-2-(2-nitrophenyl) |
| 46 | 30 | 4-[3-(ethylamino)propyl]-6,7-dihydro-4-isobutyl-2-(4-n-pentylphenyl) |

EXAMPLE 47

N,N-Dimethyl-6,7-dihydro-4-methyl-2-phenyl-4H-pyrano[4,3-d]thiazole 4-acetamide (IV; $R^1 = H$, $R^2 = CH_3$; $n = 1$ and $A = CON(CH_3)_2$)

By following the procedure of Example 2(a) but using as starting material in Example 2(a) an appropriate starting material of formula II, for example, those described in Examples 2 to 14, and appropriate ketoamide of formula III in which $R^2$ and n are as described above and A is $CONR^4R^5$ in which $R^4$ and $R^5$ are as described above, the amides listed in Examples 15 to 30 are obtained. For example, according to the present procedure 2-phenyl-4-(β-hydroxyethyl)-thiazole condensed with N,N-dimethylacetoacetamide to give the title compound, identical to the amide described in Example 15.

EXAMPLE 48

4-(2-Hydroxyethyl)-6,7-dihydro-4-methyl-2-phenyl-4H-pyrano[4,3-d]-thiazole (IV; $R^1 = H$, $R^2 = CH_3$, $n = 1$ and $A = CH_2OH$)

A solution of 6,7-dihydro-4-methyl-2-phenyl-4H-pyrano[4,3-d]thiazole4-acetic acid (15.0 g, 51.9 mmoles, described in Example 2) in dry tetrahydrofuran (200 ml) is added dropwise during 20 min to a cold solution of lithium alumium hydride (3 g) in dry tetrahydrofuran (250 ml). The mixture is stirred overnight at room temperature. Water is added dropwise with cooling and stirring, followed by the addition of magnesium sulfate. The mixture is filtered, the residue is washed with tetrahydrofuran and the filtrate is evaporated under reduced pressure to give the title compound, nmr (CDCl$_3$) δ 1.6 (s, 3H), 2.12 (t, J = 6Hz, 2H), 2.9 (m, 2H), 2.92 (s, 1H), 3.7 (t, J = 6Hz, 2H), 4.05 (m, 2H), 7.3–8.0 (m, 5H).

The corresponding hydrochloric acid addition salt (hydrochloride) of the title compound has mp 161°–162° C, after trituration with ether containing hydrogen chloride.

EXAMPLE 49

4-(2-Hydroxyethyl)-6,7-dihydro-4-methyl-2-phenyl-4H-pyrano[4,3-d]-thiazole (IV; $R^1 = H$, $R^2 = CH_3$, $n = 1$ and $A = CH_2OH$)

By following the procedure of Example 2 but using as starting material in Example 2 an appropriate starting material of formula II, for example, those described in EXamples 2 to 14, and an appropriate ketoalcohol lower alkyl ester of formula III in which $R^2$ and $n$ are as described herein and A is $CH_2OCOR^7$ in which $R^7$ is as described herein, the corresponding alcohol compounds of formula IV ($A = CH_2OH$) are obtained. For example, according to the present procedure 2-phenyl-4-(β-hydroxyethyl)thiazole condenses with 1-acetoxy-3-butanone followed by alkaline hydrolysis to give the title compound, identical to the alcohol described in Example 48.

EXAMPLE 50

4-[2-(Methylamino;ethyl]-6,7-dihydro-4-methyl-2-phenyl-4H-pyrano[4,3-d]-thiazole (I; $R^1 = H$, $R^2 = CH_3$, $R^3 = NHCH_3$ and $n = 1$)

p-Toluenesulfonyl chloride (10.3 g, 54.1 mmoles) is added to a solution of 4-[2-(hydroxy)ethyl]-6,7-dihydro-4-methyl-2-phenyl-4H-pyrano[4,3-d]thiazole hydrochloride (15.5 g, 49.7 mmoles, described in Example 48 or 49) in dry pyridine (50 ml) and the mixture is stirred at room temperature for 4 hr. After the addition of water the mixture is stirred for 1 hr and extracted with ether-chloroform.

The organic extract is washed with water, dilute hydrochloric acid, sodium bicarbonate solution and water. The organic solution is dried over sodium sulfate, treated with charcoal and evaporated under reduced pressure. The residue is triturated with hexane-ether to give 4-[2-(p-toluenesulfonyloxy)ethyl]-6,7-dihydro-4-methyl-2-phenyl-4H-pyrano[4,3-d]thiazole, mp 86°–87° C.

A mixture of 4-[2-(p-toluenesulfonyloxy)ethyl]-6,7-dihydro-4-methyl-2-phenyl-4H-pyrano[4,3-d]thiazole (16 g, 37.2 mmoles, described above), and lithium bromide (16 g) in dry acetone (100 ml) is heated at reflux temperature for 2 hr. The solvent is removed under reduced pressure, water is added and the aqueous solution is extracted with ether. The ether solution is washed with water, dried over sodium sulfate, treated with charcoal and evaporated under reduced pressure to give 4-(2-bromoethyl)-6,7-dihydro-4-methyl-2-phenyl-4H-pyrano[4,3-d]thiazole, $\gamma_{max}^{CHCl_3}$ 1545, 1500, 1465 and 1090 cm$^{-1}$.

To a solution of 4-(2-bromoethyl)-6,7-dihydro-4-methyl-2-phenyl-4H-pyrano[4,3-d]thiazole (3.14 g, 9.28 mmoles, decribed above) in dry tetrahydrofuran (50 ml), methylamine gas is slowly added during 1 hr. After standing overnight additional methylamine gas is introduced and the solution is allowed to stand for 24 hr. After evaporation under reduced pressure the residue is taken up in aqueous sodium bicarbonate solution and extracted with chloroform. The organic extract is washed with water, dried over sodium sulfate and evaporated under reduced pressure. The residue is dissolved in acetone-ether and the crystalline precipitate is removed by filtration. The filtrate is evaporated under reduced pressure to give the title compound, nmr (CDCl$_3$) δ 1.57 (s, 3H), 2.07 (+, J = 5Hz), 2.44 (s, 3H), 2.60 (m, 2H), 2.94 (+, J = 5.5 Hz), 4.10 (+, J = 5.5 Hz), 7.5–8/0 (m, 5H), identical to the amine described in Example 31.

The corresponding hydrobromic acid addition salt (dihydrobromide) of the title compound has mp 217°–220° C, after crystallization from methanol-ether By following the procedure of Examples 48, or 49 and 50 but using as starting material in Example 48 an appropriate starting material of formula I in which $R^1$, $R^2$ and $n$ are as defined herein and $R^3$ is COOH, for example the acids described in Examples 2 to 14, followed by the use of an appropriate amine of formula $NHR^4R^5$, for example the amines described in Examples 15 to 27, in the procedure of Example 50, the respective amino compound of formula I in which $R^1$, $R^2$ and $n$ are as defined herein and $R^3$ is $CH_2NR^4R^5$, for example those described in Examples 31 to 46, are obtained. For example, according to the present procedure 4-(2-hydroxyethyl)-6,7-dihydro-4-methyl-2-phenyl-4H-pyrano[4,3-d]thiazole described in Example 48) is converted using ammonia, as described above, to give the corresponding amine of formula I, 4-(2-aminoethyl)-6,7-dihydro-4-methyl-2-phenyl-4H-pyrano[4,3-d]thiazole, nmr (DMSO-$d_6$) δ 1,57 (s, 3H), 2.15 (m, 2H), 2.7 (m, 4H), 4.06 (t), J = 5.5 Hz, 2H), 7.4–8.0 (m, 5H), identical to the amine described in Example 31. The corresponding maleic acid addition salt of the latter compound has mp 144°–147° C, after crystallization from acetone-ether.

EXAMPLE 51

N-Acetyl-4-(2-aminoethyl)-6,7-dihydro-4-methyl-2-phenyl-4H-pyrano[4,3-d]thiazole (IV; $R^1$ = H, $R^2$ = $CH_3$, $n$ = 1, and A = $CH_2NHCOCH_3$)

By following the procedure of Example 2(a) but using as starting material in Example 2(a) an appropriate starting material of formula II, for example, those described in Examples 2 to 14 and an appropriate ketoamide of formula III in which $R^2$ and $n$ are as described above and A is $CH_2NR^4COR^8$ wherein $R^4$ and $R^8$ are as described above, the corresponding amides of formula IV in which $R^1$, $R^2$ and $n$ are as described above and A is $CH_2NR^4COR^8$ wherein $R^4$ and $R^8$ are as described above, are obtained. For example, according to the present procedure 2-phenyl-4-(β-hydroxyethyl)-thiazole condenses with 1-acetamido-3-butanone to give the title compound.

Reduction of the above ketoamides of formula IV, i.e. A is $CH_2NR^4COR^8$, with lithium aluminum hydride according to the procedure of Example 31 gives the corresponding amino compounds of formula I.

EXAMPLE 52

4-[2-(Dimethylamino)ethyl]-6,7-dihydro-4-methyl-2-phenyl-4H-pyrano[4,3-d]thiazole (I; $R^1$ = H, $R^2$ = $CH_3$, $R^3$ = $N(CH_3)_2$ and $n$ = 1)

By following the procedure of Example 2(a) but using as starting material in Example 2(a) an appropriate starting material of formula II, for example, those described in Examples 2 to 14 and an appropriate aminoketone of formula III in which $R^2$ and $n$ are as described above and A is $CH_2NR^4R^5$ wherein $R^4$ and $R^5$ are as described above, the amino compounds of formula I listed in Examples 31 to 46 are obtained. For example, according to the present procedure 2-phenyl-4-(β-hydroxyethyl)thiazole condenses with 1-(N,N-dimethylamino)-3-butanone to give the title compound, identical to the amine described in Example 31.

We claim:

1. A compound of formula I

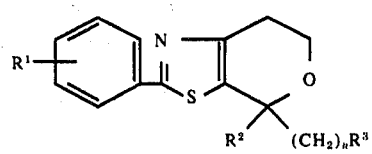

in which $R^1$ is hydrogen, halogen, lower alkyl, lower alkoxy or nitro; $R^2$ is lower alkyl; $R^3$ is COOH or $CH_2NR^4R^5$ in which $R^4$ and $R^5$ are the same or different selected from the group consisting of hydrogen and lower alkyl; and $n$ is the integer one or two; or a pharmaceutically acceptable salt thereof.

2. 6,7-Dihydro-4-ethyl-2-phenyl-4H-pyrano[4,3-d]thiazole-4-acetic acid, as claimed in claim 1.

3. 6,7-Dihydro-4-methyl-2-phenyl-4H-pyrano[4,3-d]thiazole-4-acetic acid, as claimed in claim 1.

4. 6,7-Dihydro-4-methyl-2-phenyl-4H-pyrano[4,3-d]thiazole-4-propionic acid, as claimed in claim 1.

5. 6,7-Dihydro-4-(n-propyl)-2-phenyl-4H-pyrano[4,3-d]thiazole-4-acetic acid, as claimed in claim 1.

6. 6,7-Dihydro-4-methyl-2-(p-chlorophenyl)-4H-pyrano[4,3-d]thiazole-4-acetic acid, as claimed in claim 1.

7. 6,7-Dihydro-4-ethyl-2-(p-chlorophenyl)-4H-pyrano[4,3-d]thiazole-4-acetic acid, as claimed in claim 1.

8. 4-[2-(Dimethylamino)ethyl]-6,7-dihydro-4-methyl-2-phenyl- 4H-pyrano[4,3-d]thiazole, as claimed in claim 1.

9. 4-(3-Aminopropyl)-6,7-dihydro-4-methyl-2-phenyl -4H-pyrano-[4,3-d]thiazole, as claimed in claim 1.

10. 4-[3-(Dimethylamino)propyl]-6,7-dihydro-4-methyl-2-phenyl-4H-pyrano[4,3-d]thiazole, as claimed in claim 1.

11. 4-[2-Methylamino)ethyl]-6,7-dihydro-4-methyl-2-phenyl-4H-pyrano[4,3-d]thiazole, as claimed in claim 1.

12. 4-(2-Aminoethyl)-6,7-dihydro-4-methyl-2-phenyl-4H-pyrano[4,3-d]thiazole, as claimed in claim 1.

13. A compound of formula IV

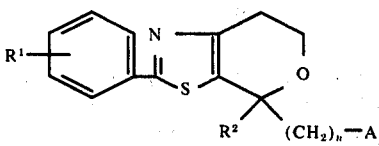

in which $R^1$ is hydrogen, halogen, lower alkyl, lower alkoxy or nitro, $R^2$ is lower alkyl; $n$ is the integer one or two; and A is selected from the group consisting of $COOR^6$ in which $R^6$ is lower alkyl, $CONR^4R^5$ in which $R^4$ and $R^5$ are the same or different selected from the group consisting of hydrogen and lower alkyl, $CH_2OCOR^7$ in which $R^7$ is lower alkyl, and $CH_2NR^4COR^8$ in which $R^4$ is as defined herein and $R^8$ is an alkyl containing one to five carbons.

14. A compound of formula I

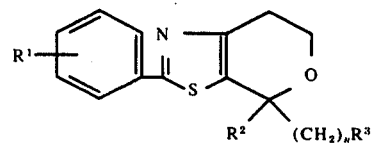

in which $R^1$ is hydrogen or halogen; $R^2$ is lower alkyl; $R^3$ is COOH or $CH_2NR^4R^5$ in which $R^4$ and $R^5$ are the same or different selected from the group consisting of hydrogen or lower alkyl; and $n$ is the integer one or two; or a pharmaceutically acceptable salt thereof.

15. A compound of formula IV

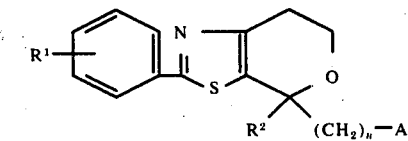

in which $R^1$ is hydrogen or halogen; $R^2$ is lower alkyl; $n$ is the integer one or two; and A is selected from the group consisting of $COOR^6$ in which $R^6$ is lower alkyl and $CONR^4R^5$ in which $R^4$ and $R^5$ are the same or different selected from the group of hydrogen and lower alkyl.

16. A process for preparing a compound of formula I

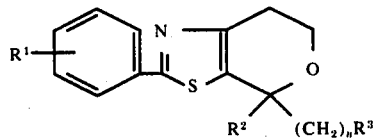

in which $R^1$ is hydrogen, halogen, lower alkyl, lower alkoxy or nitro; $R^2$ is lower alkyl; $R^3$ is COOH and $n$ is the integer 1 or 2, which comprises:

a. condensing a compound of formula II

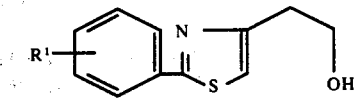

in which $R^1$ is as defined herein with a compound of formula

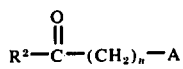

in which $R^2$ is lower alkyl, $n$ is the integer 1 or 2 and A is $COOR^6$ in which $R^6$ is lower alkyl, in the presence of an acid catalyst, to obtain the corresponding compound of formula IV

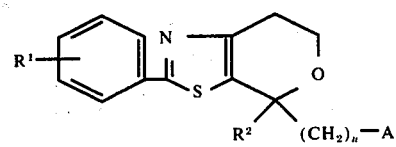

in which $R^1$ and $R^2$ are as defined herein and A is $COOR^6$ in which $R^6$ is lower alkyl, and subjecting the last-named compound to hydrolysis to obtain the corresponding compound of formula I in which $R^3$ is COOH.

17. A process for preparing a compound formula I

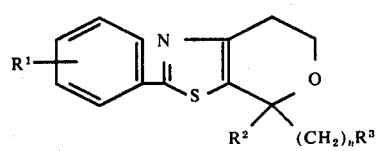

in which $R^1$ is hydrogen, halogen, lower alkyl, lower alkoxy or nitro; $R^2$ is lower alkyl; $R^3$ is $CH_2NR^4R^5$ in which $R^4$ and $R^5$ are the same or different selected from the group consisting of hydrogen and lower alkyl; and $n$ is the integer 1 or 2, which comprises:

a. condensing a compound of formula II

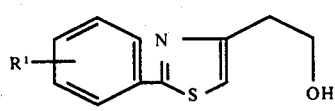

in which $R^1$ is as defined herein with a compound of formula

in which $R^2$ is lower alkyl, $n$ is the integer 1 or 2 and A is $COOR^6$ in which $R^6$ is lower alkyl, in the presence of an acid catalyst, to obtain the corresponding compound formula IV

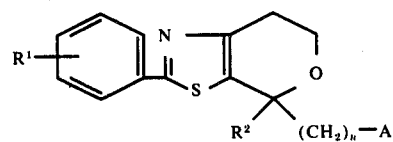

in which $R^1$ and $R^2$ are as defined herein and A is $COOR^6$ in which $R^6$ is lower alkyl, and subjecting the last-named compound to hydrolysis to obtain the corresponding compound of formula IV in which A is COOH, subjecting the last-named product to amidation with an appropriate amine of formula $NHR^4R^5$ in which $R^4$ and $R^5$ are as defined herein to give the corresponding compound of formula IV in which A is $CONR^4R^5$, and reducing the last-named compound with a complex metal hydride to give the corresponding compound of formula I in which $R^1$ and $R^2$ are as defined herein and $R^3$ is $CH_2NR^4R^5$ as defined herein.

* * * * *